(12) United States Patent
Zou et al.

(10) Patent No.: US 9,836,859 B2
(45) Date of Patent: Dec. 5, 2017

(54) WIDE X-RAY SPECTRUM PHOTON COUNTING COMPUTED TOMOGRAPHY

(71) Applicant: TOSHIBA MEDICAL SYSTEMS CORPORATION, Otawara-shi (JP)

(72) Inventors: Yu Zou, Naperville, IL (US); Zhou Yu, Palatine, IL (US); Yuexing Zhang, Naperville, IL (US); Xiaolan Wang, Buffalo Grove, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 128 days.

(21) Appl. No.: 14/593,784

(22) Filed: Jan. 9, 2015

(65) Prior Publication Data

US 2016/0203620 A1    Jul. 14, 2016

(51) Int. Cl.
| | |
|---|---|
| *G01N 23/00* | (2006.01) |
| *G06T 11/00* | (2006.01) |
| *G01N 23/04* | (2006.01) |
| *G01N 23/087* | (2006.01) |
| *G01T 1/16* | (2006.01) |
| *G01T 7/00* | (2006.01) |
| *G01T 1/29* | (2006.01) |
| *A61B 6/03* | (2006.01) |

(52) U.S. Cl.
CPC ............ *G06T 11/003* (2013.01); *A61B 6/032* (2013.01); *G01N 23/046* (2013.01); *G01N 23/087* (2013.01); *G01T 1/1606* (2013.01); *G01T 1/2985* (2013.01); *G01T 7/005* (2013.01)

(58) Field of Classification Search
None
See application file for complete search history.

(56) References Cited

U.S. PATENT DOCUMENTS

| | | | | |
|---|---|---|---|---|
| 4,097,793 A | * | 6/1978 | Shapiro | H05G 1/265 324/403 |
| 4,168,436 A | * | 9/1979 | Aradate | A61B 6/032 378/101 |
| 4,532,644 A | * | 7/1985 | Yamaguchi | A61B 6/032 378/106 |
| 4,614,999 A | * | 9/1986 | Onodera | H05G 1/20 363/28 |
| 5,434,900 A | * | 7/1995 | Tanaka | A61B 6/56 378/15 |
| 7,505,550 B2 | * | 3/2009 | Goto | A61B 6/032 378/4 |
| 7,715,520 B2 | * | 5/2010 | Nagata | A61B 6/032 378/16 |
| 8,031,831 B2 | | 10/2011 | Zou | |
| 9,014,336 B2 | * | 4/2015 | Luerkens | H05G 1/10 378/106 |

(Continued)

OTHER PUBLICATIONS

Kalender, et al., "Application- and patient size-dependent optimization of x-ray spectra for CT", Medical Physics 36, 993 (2009); http://dx.doi.org/10.1118/1.3075901.

*Primary Examiner* — Andrew Smyth

(74) *Attorney, Agent, or Firm* — Oblon, McClelland, Maier & Neustadt, L.L.P.

(57) ABSTRACT

A computed tomography (CT) imaging apparatus includes a radiation source configured to emit X-rays; a plurality of photon-counting detectors configured to detect X-rays emitted by the radiation source and generate a photon counting signal based on the detected X-rays; and processing circuitry to obtain a kV-waveform used by the radiation source to generate the X-rays during a scan of an object, and adjust at least one energy threshold dividing the photon counting signal into a plurality of spectra bins in accordance with the obtained kV-waveform.

20 Claims, 11 Drawing Sheets

(56) References Cited

U.S. PATENT DOCUMENTS

| | | | |
|---|---|---|---|
| 2005/0185759 A1* | 8/2005 | Toth | A61B 6/032 378/109 |
| 2006/0109949 A1* | 5/2006 | Tkaczyk | A61B 6/032 378/4 |
| 2007/0053483 A1* | 3/2007 | Nagata | A61B 6/032 378/8 |
| 2007/0189436 A1* | 8/2007 | Goto | A61B 6/032 378/4 |
| 2007/0237288 A1* | 10/2007 | Tkaczyk | A61B 6/032 378/5 |
| 2011/0116697 A1* | 5/2011 | Dafni | G06T 11/008 382/131 |
| 2012/0087463 A1* | 4/2012 | Greenberg | G01T 7/005 378/5 |
| 2012/0163557 A1* | 6/2012 | Hsieh | A61B 6/032 378/207 |
| 2013/0251096 A1* | 9/2013 | Hiraoka | A61B 6/503 378/8 |
| 2013/0251097 A1* | 9/2013 | Zou | A61B 6/032 378/9 |
| 2013/0251108 A1* | 9/2013 | Luerkens | H05G 1/10 378/106 |
| 2013/0336443 A1* | 12/2013 | Gagnon | A61B 6/032 378/19 |
| 2014/0014828 A1* | 1/2014 | Bredno | A61B 6/032 250/252.1 |
| 2014/0105354 A1* | 4/2014 | Gagnon | A61B 6/032 378/19 |

\* cited by examiner

WIDE X-RAY SPECTRUM PHOTON COUNTING COMPUTED TOMOGRAPHY

FIELD

Embodiments disclosed herein generally relate photon-counting computed tomography (CT) systems and CT systems with dual X-ray tubes.

BACKGROUND

Traditional CT scanners use energy-integrating detectors for acquiring energy integration X-ray data. An energy-integrating detector does not take advantage of the energy information in the X-ray beam. Even though the X-ray source emits X-rays in a broad spectrum, the detector is not able to differentiate between photons of different energy, but delivers an output signal proportional to the total energy of the photons registered during the readout interval. To obtain the spectral nature of the transmitted X-ray data, a photon-counting detector splits the X-ray beam into its component energies or spectrum bins and counts a number of photons in each of the bins. The use of the spectral nature of the X-ray source in CT is often referred to as spectral CT. Spectral CT imaging provides material separation capabilities that can potentially enable new clinical applications. The spectral images are usually presented as material concentration images of basis materials or monoenergetic images. For example, spectral CT is used in discriminating tissues, differentiating between materials such as tissues containing calcium and iodine, or enhancing the detection of smaller vessels. Among other advantages, spectral CT is also expected to reduce beam-hardening artifacts and to increase accuracy in CT numbers independent of scanners.

Currently, most conventional designs acquire spectral information using either high- and low-energy X-ray sources or dual-detector-layer technologies. To improve the accuracy of material separation, photon counting detector technologies can be used to provide good energy resolution. Photon-counting energy-resolved direct-conversion semiconductor detectors for computed tomography (CT) allow exploitation of the spectral information of each incident photon. X-ray photons interacting with the semiconductor sensors can be converted directly to electron-hole pairs without any inefficient intermediate processes, ensuring the superior intrinsic energy resolution.

One of the key obstacles in performing a CT image reconstruction is the ability to make the noise uniform. In a conventional CT system, the noise is generally non-uniformly distributed in 3D space. In spectral CT, a monoenergetic image has an additional dimension along energy. Therefore, improving noise non-uniformity along the energy direction via X-ray source control is a challenge in spectral CT image reconstruction. For example, for the conventional kV switching technology, it is difficult to modulate mA levels between the two kVs, resulting in non-uniform noise in the energy direction.

BRIEF DESCRIPTION OF THE DRAWINGS

A more complete appreciation of the disclosed inventions and the many attendant advantages thereof will be readily obtained as the same becomes better understood by reference to the following detailed description when considered in connection with the accompanying drawings, wherein.

DETAILED DESCRIPTION

A hybrid-geometry photon-counting CT (PCCT) system was described in U.S. patent application Ser. No. 13/426,903. In the hybrid PCCT design, a ring of sparsely distributed photon-counting detectors is used to acquire spectral information in a fourth-generation CT geometry, while energy-integrating detectors acquire data using a third-generation geometry. The fourth-generation design can overcome challenges facing photon-counting detector technology, while the third-generation data can be used to maintain the spatial resolution and noise characteristics of the reconstruction.

In photon-counting CT, the spectral information is measured by the PCD detectors. Therefore, it is possible to use the X-ray source modulation as an additional tool to achieve better noise uniformity across all energies.

In one embodiment, there is provided a computed tomography (CT) imaging apparatus, comprising: (1) a plurality of photon-counting detectors configured to detect X-rays emitted by the radiation source and generate a photon counting signal based on the detected X-rays; and
(2) processing circuitry configured to obtain a kV-waveform used by the radiation source to generate the X-rays during a scan of an object, and adjust at least one energy threshold dividing the photon counting signal into a plurality of spectra bins in accordance with the obtained kV-waveform.

In another embodiment, there is provided a computed tomography (CT) imaging method, comprising: (1) obtaining a kV-waveform used by a radiation source to generate X-rays during a scan of an object; and (2) adjusting at least one energy threshold dividing a photon counting signal obtained from a photon-counting detector into a plurality of spectra bins in accordance with the obtained kV-waveform.

In accordance with an exemplary embodiment, while a method and system for generating a wide X-ray spectrum in an medical image generated by an medical imaging system is described and discussed herein below with reference to a computed tomography (CT) imaging system, it should be understood that the method and system of the invention may be applied to other imaging systems with photon counting detectors.

Figure 1:
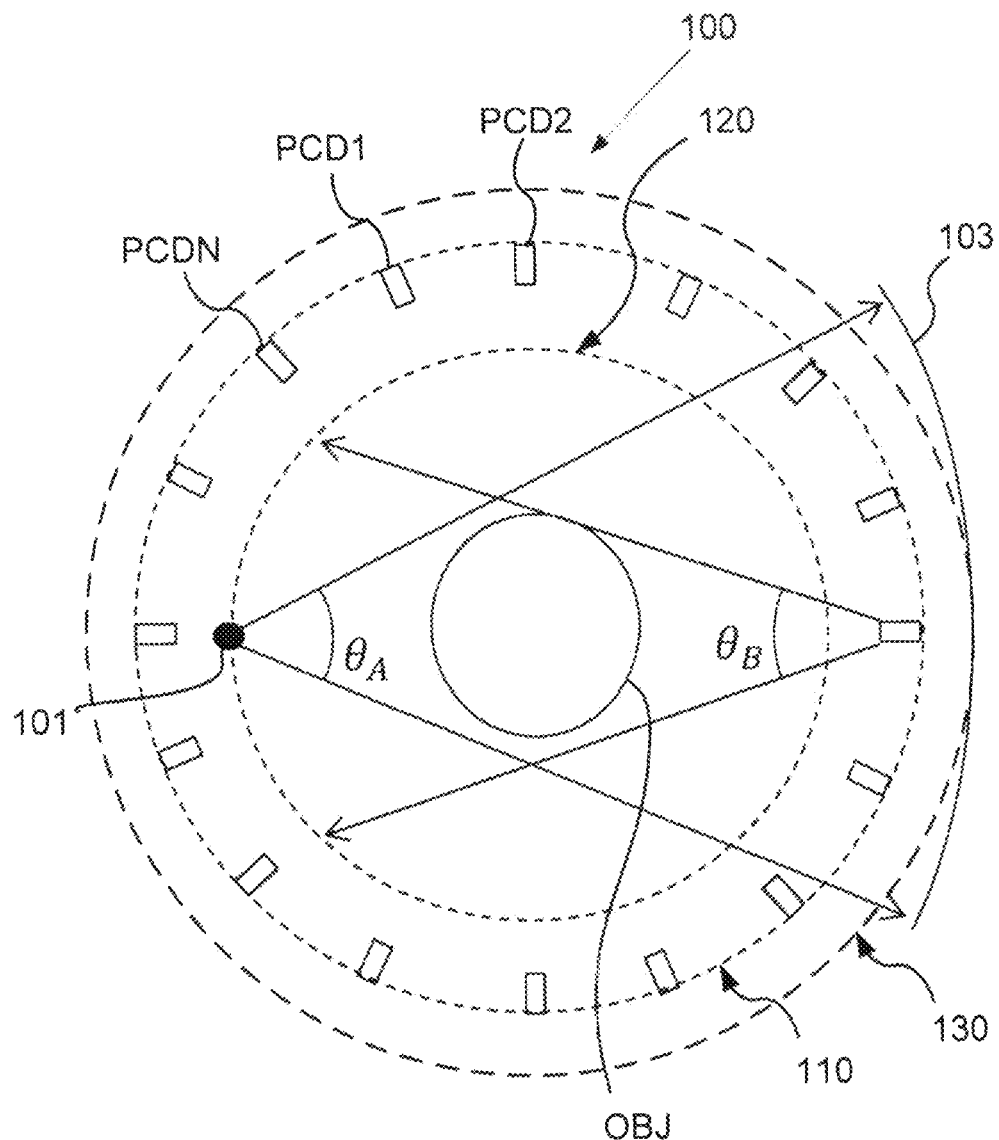
FIG. 1 is a diagram of a cross-section of a combined third-generation and fourth-generation computed tomography apparatus, according to one embodiment.

Referring now to the drawings, wherein like reference numerals designate identical or corresponding parts throughout the several views, FIG. 1 is a diagram illustrating an implementation for placing the photon-counting detectors (PCDs) having a predetermined fourth-generation geometry in combination with a detector having a predetermined third-generation geometry in a CT scanner system. The diagram illustrates relative positions among an object OBJ to be scanned, an X-ray source 101, an X-ray detector 103, and the photon-counting detectors PCD1-PCDN, in one exemplary embodiment. For the sake of simplicity, the diagram excludes other components and circuits that may be used in acquiring and processing data as well as reconstructing an image based upon the acquired data. In general, the photon-counting detectors PCD1-PCDN each output a photon count for each predetermined energy bin. In addition to the sparse photon-counting detectors PCD1-PCDN in the fourth-generation geometry, the implementation shown in FIG. 1 includes a detector, such as the detector 103, having a conventional third-generation geometry in the CT scanner system. The detector elements in the detector 103 can be more densely placed along the detector surface than the photon-counting detectors, PCD1-PCDN. See related U.S. application Ser. No. 13/426,903, the contents of which are incorporated herein by reference.

In one implementation, the photon-counting detectors PCD1-PCDN are sparsely placed around the object OBJ in a predetermined geometry such as a circle. For example, the photon-counting detectors PCD1-PCDN are fixedly placed on a predetermined circular component 110 in the gantry 100. In one implementation, the photon-counting detectors PCD1-PCDN are fixedly placed on the circular component 110 at predetermined equidistant positions. In an alternative implementation, the photon-counting detectors PCD1-PCDN are fixedly placed on the circular component 110 at predetermined non-equidistant positions. The circular component 110 remains stationary with respect to the object OBJ and does not rotate during the data acquisition.

Both the X-ray source 101 and the detector 103 rotate around the object OBJ while the photon-counting detectors PCD1-PCDN are stationary with respect to the object OBJ. In one implementation, the X-ray source 101 is mounted on a first rotating portion 120 of the annular frame in the gantry 100 so that the X-ray source 101 projects X-ray radiation with a predetermined source fan beam angle $\theta_A$ towards the object OBJ while the X-ray source 101 rotates around the object OBJ inside the sparsely placed photon-counting detectors PCD1-PCDN. Furthermore, an additional detector 103 is mounted on a second rotating portion 130 having the third-generation geometry. The rotating portion 130 mounts the detector 103 at a diametrically opposed position from the X-ray source 101 across the object OBJ and rotates outside the stationary circular component 110, on which the photon-counting detectors PCD1-PCDN are fixedly placed in a predetermined sparse manner.

In one implementation, the rotating portions 120 and 130 are integrally constructed as a single component to maintain a fixed angle (such as a 180-degree angle) between the X-ray source 101 and the detector 103 as they rotate about the object OBJ with a different radius. In an optional implementation, the rotating portions 120 and 130 are separate components, but synchronously rotate to maintain the X-ray source 101 and the detector 103 in the fixedly opposed positions at 180-degrees across the object OBJ. Furthermore, the X-ray source 101 optionally travels a helical path as the object is moved in a predetermined direction that is perpendicular to the rotational plane of the rotating portion 120.

As the X-ray source 101 and the detector 103 rotate around the object OBJ, the photon-counting detectors PCD1-PCDN and the detector 103, respectively detect the transmitted X-ray radiation during data acquisition. The photon-counting detectors PCD1-PCDN intermittently detect with a predetermined detector fan beam angle $\theta_B$ the X-ray radiation that has been transmitted through the object OBJ and each individually output a count value representing a number of photons, for each of predetermined energy bins. On the other hand, the detector elements in the detector 103 continuously detect the X-ray radiation that has been transmitted through the object OBJ and output the detected signals as the detector 103 rotates. In one implementation, the detector 103 has densely placed energy-integrating detectors in predetermined channel and segment directions on the detector surface.

In one implementation, the X-ray source 101, the photon-counting detectors PCD1-PCDN and the detector 103 collectively form three predetermined circular paths that differ in radius. The photon-counting detectors PCD1-PCDN are sparsely placed along a first circular path around the object OBJ while at least one X-ray source 101 rotates along a second circular path around the object OBJ. Further, the detector 103 travels along a third circular path. The above exemplary embodiment illustrates that the third circular path is the largest and outside the first and second circular paths around the object OBJ. Although not illustrated, an alternative embodiment optionally changes the relative relation of the first and second circular paths so that the second circular path for the X-ray source 101 is larger and outside the first circular path of the sparsely placed photon-counting detectors PCD1 through PCDN around the object OBJ. Furthermore, in another alternative embodiment, the X-ray source 101 also optionally travels on the same third circular path as the detector 103. Furthermore, the above alternative embodiments optionally provide a protective rear cover for each of the photon-counting detectors PCD1-PCDN that are irradiated from behind as the X-ray source 101 travels outside the first circular path of the sparsely placed photon-counting detectors PCD1-PCDN.

There are other alternative embodiments for placing the photon-counting detectors having a predetermined fourth-generation geometry in combination with the detector having a predetermined third-generation geometry in the CT scanner. An embodiment optionally includes the X-ray source 101, which is configured to or designed to perform a kV-switching function for emitting X-ray radiation at a predetermined high-level energy and at a predetermined low-level energy.

In general, the photon-counting detectors PCD1-PCDN are sparsely positioned along the circular component 110. Although the photon-counting detectors PCD1-PCDN acquire sparse view projection data, the acquired projection data is sufficient for at least dual-energy (DE) reconstruction with a sparse view reconstruction technique. In addition, the detector 103 also acquires another set of projection data, which is used to generally improve image quality. In the case that the detector 103 consists of energy-integrating detectors with anti-scatter grids, the projection data from the detector 103 is used to correct scatter on the projection data from the photon-counting detectors PCD1-PCDN. In one implementation, the integrating detectors optionally need to be calibrated in view of X-ray transmission through the predetermined circular component 110 and some of the photon-counting detectors PCD1-PCDN. In acquiring the projection data, a sampling on the source trajectory is optionally made sufficiently dense in order to enhance spatial resolution.

Figure 2:
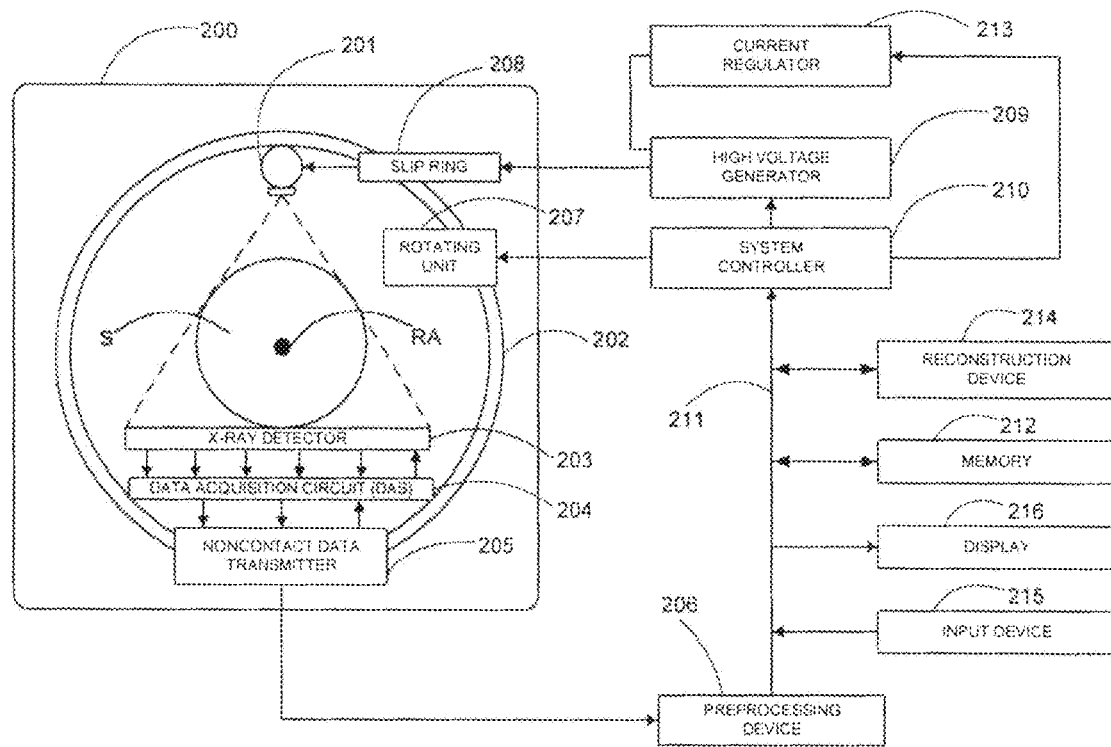
FIG. 2 illustrates an implementation of a computed tomography system, according to one embodiment.

FIG. 2 illustrates an implementation of the radiography gantry 100 of FIG. 1 in a CT apparatus or scanner. As shown in FIG. 2, a radiography gantry 200 is illustrated from a side view and further includes an X-ray tube 201, an annular frame 202, and a multi-row or two-dimensional-array-type X-ray detector 203. The X-ray tube 201 and X-ray detector 203 are diametrically mounted across a subject S on the annular frame 202, which is rotatably supported around a rotation axis RA. A rotating unit 207 rotates the annular frame 202 at a high speed, such as 0.4 sec/rotation, while the subject S is being moved along the axis RA into or out of the illustrated page.

The multi-slice X-ray CT apparatus further includes a high voltage generator 209 that generates a tube voltage applied to the X-ray tube 201 through a slip ring 208 so that the X-ray tube 201 generates X-rays. The X-rays are emitted towards the subject S, whose cross sectional area is represented by a circle. The X-ray detector 203 is located at an opposite side from the X-ray tube 201 across the subject S for detecting the emitted X-rays that have transmitted through the subject S. The X-ray detector 203 further includes individual detector elements or units.

With continued reference to FIG. 2, the CT apparatus further includes other devices for processing the detected signals from X-ray detector 203. A data acquisition circuit or a Data Acquisition System (DAS) 204 converts a signal output from the X-ray detector 203 for each channel into a voltage signal, amplifies the signal, and further converts the signal into a digital signal. The X-ray detector 203 and the DAS 204 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 206, which is housed in a console outside the radiography gantry 200 through a non-contact data transmitter 205. The preprocessing device 206 performs certain corrections, such as sensitivity correction on the raw data. A memory 212 stores the resultant data, which is also called projection data at a stage immediately before reconstruction processing. The memory 212 is connected to a system controller 210 through a data/control bus 211, together with a reconstruction device 214, input device 215, and display 216.

The detectors are rotated and/or fixed with respect to the patient among various generations of the CT scanner systems. The above-described CT system is an example of a combined third-generation geometry and fourth-generation geometry system. In the third-generation system, the X-ray tube 201 and the X-ray detector 203 are diametrically mounted on the annular frame 202 and are rotated around the subject S as the annular frame 202 is rotated about the rotation axis RA. In the fourth-generation geometry system, the detectors are fixedly placed around the patient and an X-ray tube rotates around the patient.

In an alternative embodiment, the radiography gantry 200 has multiple detectors arranged on the annular frame 202, which is supported by a C-arm and a stand.

Figure 3:
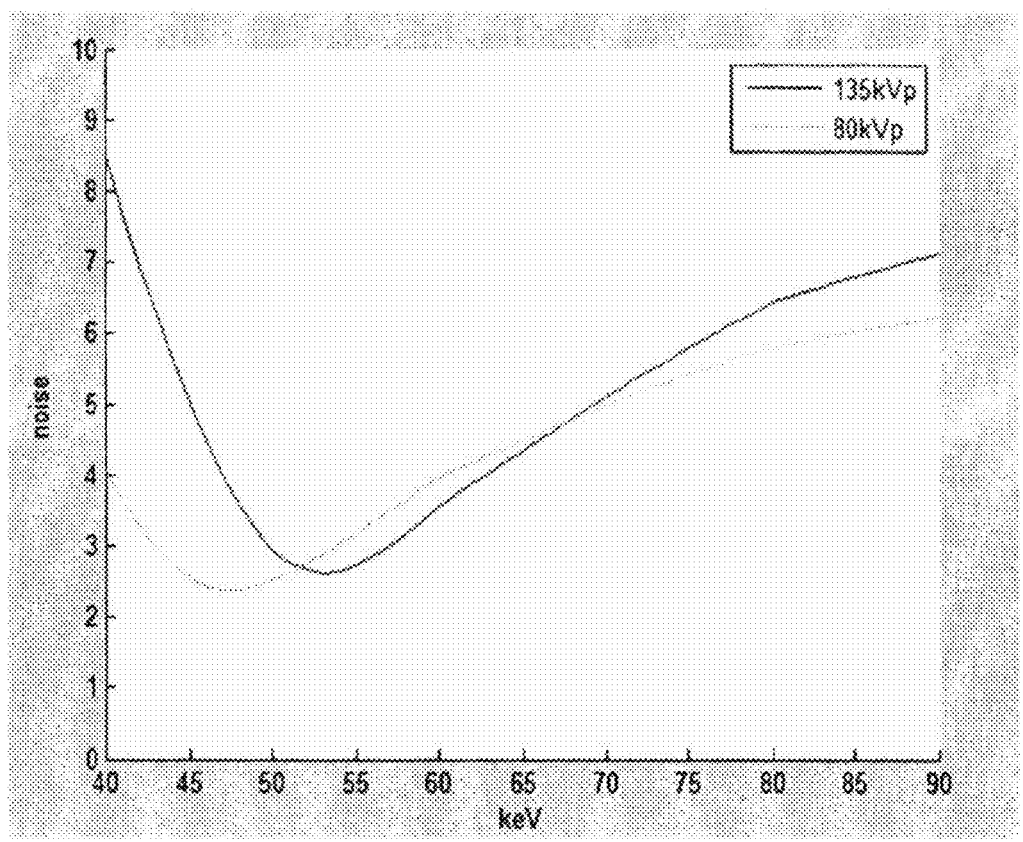
FIG. 3 shows an exemplary graph of energy vs. noise for a spectrum scan.

In spectral CT, the energy distribution of photons determines the noise distribution in monoenergetic images. If more photons are detected around a certain energy level, a lower noise will be observed in the monoenergetic image of the corresponding energy. To illustrate this phenomenon, FIG. 3 shows the noise distribution in each monoenergetic image for two source spectrums (i.e., kVps). The x-axis is the keV of the monoenergetic image, and the y-axis is the noise standard deviation of the monoenergetic image. Each curve presents a spectral CT scan, one with the tube at 135 kV, the other at 80 kV. Assuming photon-counting detectors are used, and splitting each acquisition into dual energy bins, the data domain decomposition leads to the noise results shown in FIG. 3 for the virtual monoenergetic images. As illustrated in FIG. 3, the noise is not uniformly distributed across monoenergetic images. For each source spectrum, there is a keV that has the lowest noise, while the noise increases rapidly as the monoenergetic image moves away from this optimal noise point. The range of keVs with low noise is also very narrow. It is desirable to make the noise more uniform across keVs, so that the low-noise keV range will be wider.

Figure 4:
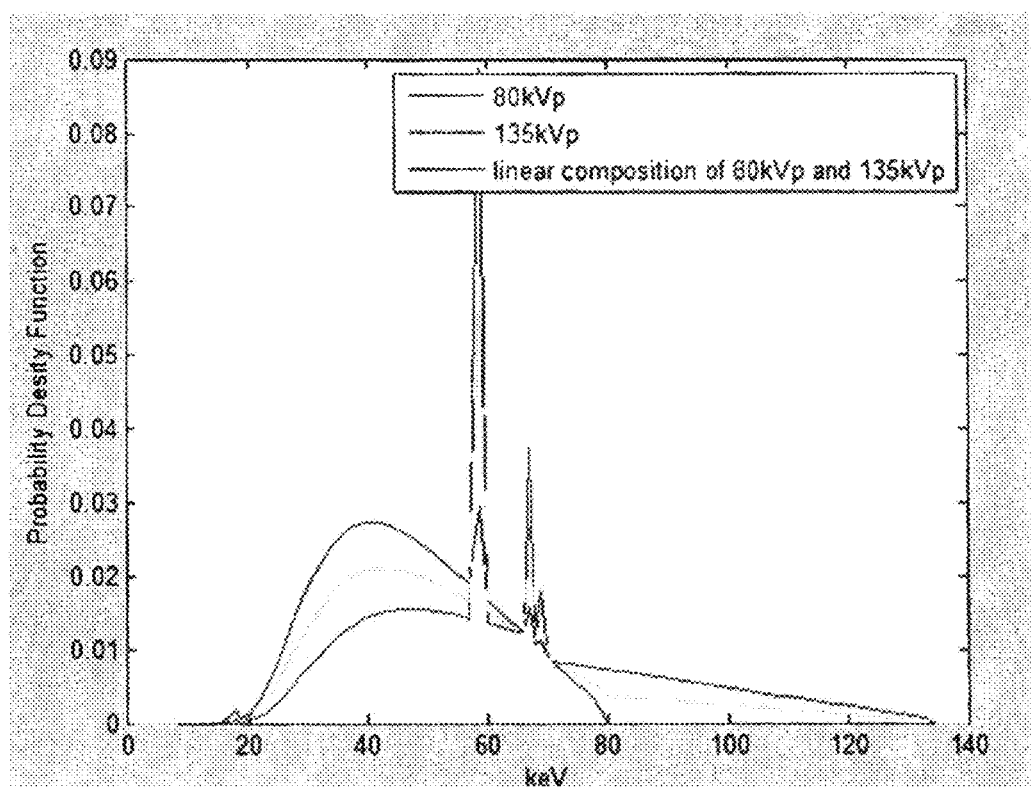
FIG. 4 shows an exemplary energy vs. probability density function for a spectrum scan.

In current X-ray source technologies, the X-ray spectrum is mainly controlled by the kVp. Therefore, a wide X-ray spectrum can be achieved by varying the kVp as a function of time. Ideally, if the X-ray source can vary kVp rapidly within one view, a wide spectrum can be obtained for that view. FIG. 4 shows that when combining an 80 kVp and a 135 kVp spectrum linearly together, the combined spectrum has more evenly distributed photons across the energy range than the photon distribution in the 80 kVp spectrum or the 135 kVp spectrum. In current tube technology, it is difficult to perform fast kVp variation. However, even a slower variation would allow the system to obtain a wider averaged X-ray spectrum. Exemplary embodiments are presented to generate a wide X-ray spectrum to achieve a more uniform noise distribution in the monoenergetic images.

Figure 5:
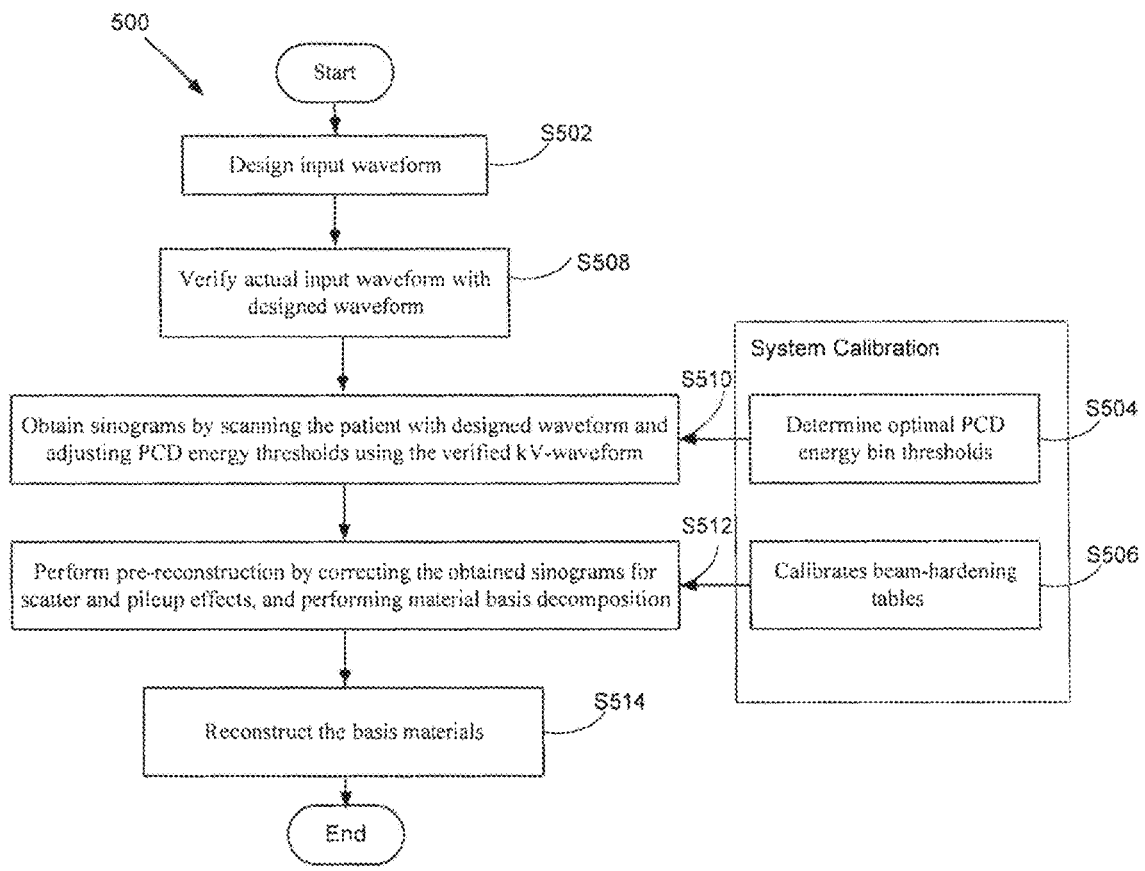
FIGS. 5 and 6 illustrate wide-spectrum enablement methods by way of flowcharts.

Referring to FIG. 5, a flowchart 500 illustrates a method for generating a wide X-ray spectrum in a third-generation CT with a hybrid detector or a hybrid-geometry photon-counting CT without an actual kV-waveform tracking function. This method can be applied to the CT system with dual X-ray tubes.

Figure 7A:
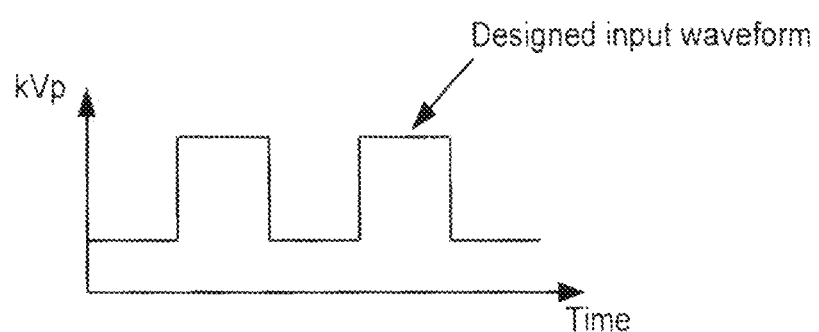
FIG. 7A illustrates an exemplary designed kVp p waveform.

In step 502, a kV and mA waveform is designed to optimize the quality of the scan for a given patient using personal information, such as age, size, gender, and the diagnostic task. The kV waveform is the defined as the input potential (kV) applied to the X-ray tube. One choice of the kV-waveform design is a square waveform composed of low and high kVs, where the waveform is specified by the ratio of high/low kV and the frequency of the switching, as shown in FIG. 7A. The low KV level is different from the high KV level. For example, in one embodiment, one can switch between 80 kVp and 140 kVp every 100 views. A more sophisticated design uses an elliptical shape to model the patient size, where the parameters of the ellipse can be found using the SFOV and the anatomy of the scan. In addition, using the body habitus measured during a pre-scan (scanogram) can be used in the waveform design.

In step 504, during system calibration, the processing circuitry determines optimal photon-counting detector (PCD) energy bin thresholds for each kV value used, so that the noise of the measurement in each bin is equalized on average of energy ranges. This can be done using either simulation or phantom measurements with high energy resolution. In other words, in this step, the energy ranges of each bin are set.

In step 506, during the system calibration, the processing circuitry calibrates beam-hardening tables for all desired kV and transition states.

Figure 7B:
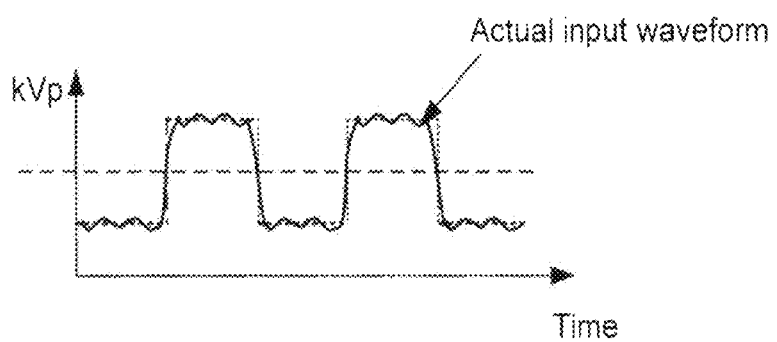
FIG. 7B illustrates an exemplary actual kVp waveform.

In step 508, the processing circuitry verifies the actual kV and mA waveform in comparison with the designed kV and mA waveform using an air scan. As shown in FIG. 7B, the actual generated kV and mA waveform is not a perfect square pulse as the designed waveform of FIG. 7A due to limitations of the waveform generator and loss in the system. This step is conducted when the system hardware is not able to record the kV-waveform in real time during a scan. Good repeatability of the kV-waveform is required. The kV-waveform verification can be done with a low-mA air scan, with the particular kV-waveforms determined in the pre-scan design, before or after the patient scan. Alternatively, a reference photon counting detector can be used to measure the spectra. The photon-counting detectors are used to record the spectra of the X-ray at every view. After correction for the detector response, the actual kV-waveform is obtained. The obtained kV and mA waveform are verified by the processing circuitry in comparison with the designed kV and mA waveforms.

In step 510, the processing circuitry obtains sinograms by scanning the patients using the designed kV-waveform, and adjusts the PCD energy thresholds for the verified kV-waveform. The thresholds are adjusted according to a pre-determined method or a user-inputted method. The energy thresholds divide the photon-counting signal into a plurality of spectra bins in accordance with the obtained KV-waveform. The energy thresholds can be adjusted to obtain equal detected photon counts in the energy bins, or equal energy intervals, or according to K-edge positions of energy in K-edge imaging.

Figure 8:
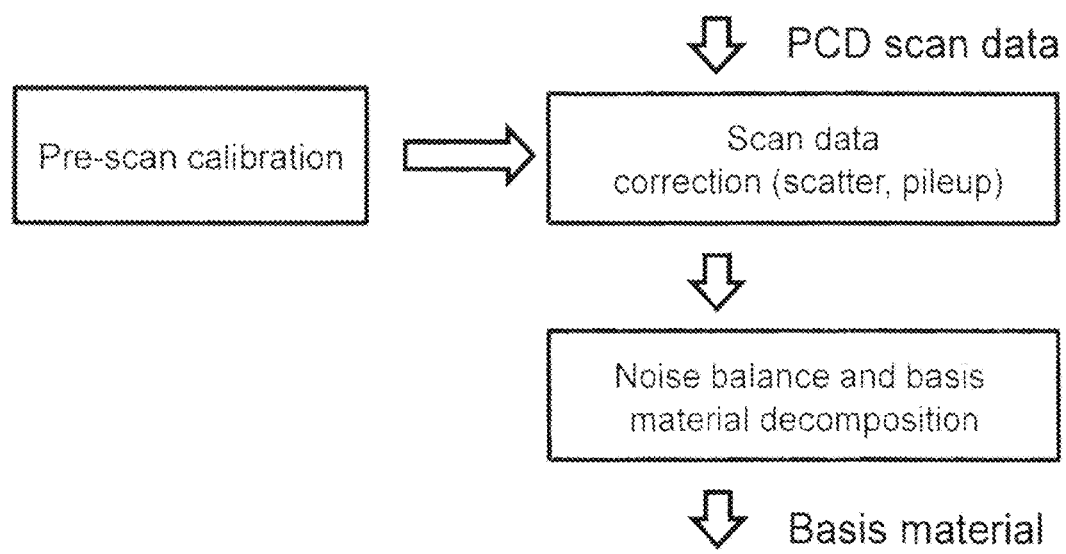
FIG. 8 illustrates exemplary pre-reconstruction processing.

In step 512, the processing circuitry performs pre-reconstruction by correcting the sinograms for scatter and pileup effects, and performing material basis decomposition in the projection domain, based on the divided spectra bins, verified kV-waveform and calibrated beam-hardening tables. As shown in FIG. 8, for every ray, the scanned spectral data from a photon-counting detector are corrected for scatter and pileup, weighted for noise balance, and decomposed into basis materials. The noise balance is weighted according to the method described in equation (3)-(5).

The scatter and pileup correction uses incident spectrum information from the kV-waveform. The scan data correction is implemented by:

$$S_{corr}(E) = S_{raw}(E) - S_{0,sct}(E) - S_{1,p,sct}(E) \quad (1)$$

wherein $S_{raw}(E)$ is raw PCD scan data, $S_{0,sct}(E)$ is a linear detector response scatter component, $S_{1,p,sct}(E)$ is a nonlinear detector response of pileup and scatter component, and E is an energy variable.

After the scan correction is complete, the projection data is calculated based on the corrected scan data using:

$$g_E = \ln(S_{corr}^{air}(E) - S_{corr}(E)) \quad (2)$$

wherein $S_{corr}(E)$ is scan-corrected data for the object to be imaged and $S_{corr}^{air}(E)$ is an air reference data (or reference data from any known object, e.g., water).

The projection data with high or low spectra along path 1 are calculated by weighting $g_E$ with a noise-balance weighting coefficient according to equations (3) and (4):

$$g_L = \Sigma_E w_E^L g_E \quad (3)$$

$$g_H = \Sigma_E w_E^H g_E \quad (4)$$

wherein $w_E^H$ is a noise balance weight for high spectra, and $w_E^L$ is a noise balance weight for low spectra.

The weight values w are defined to implement denoising and are determined for each of a corresponding material basis n and an energy spectrum m. The weights w are defined according to equation (5):

$$w_{nm} = K_n \frac{\overline{\mu_{mn}}}{\sigma_m^2} \quad (5)$$

where $k_n$ is a normalization factor for a particular material basis, $\overline{\mu_{mn}}$ is an average attenuation coefficient for basis material n and energy m, and $\sigma_m^2$ is the noise of the measured projection $g_m$. The normalization factor $k_n$ is defined according to equation (6):

$$\frac{1}{K_n} = \sum_{m=1}^{M} \frac{\overline{\mu_{mn}}}{\sigma_m^2} \quad (6)$$

The basis material decomposition is implemented using equation (7):

$$\begin{bmatrix} g_L + g_L^{BH}(L_1, L_2) \\ g_H + g_H^{BH}(L_1, L_2) \end{bmatrix} = \begin{bmatrix} \overline{\mu}_L^1 & \overline{\mu}_L^2 \\ \overline{\mu}_H^1 & \overline{\mu}_H^2 \end{bmatrix} \begin{bmatrix} L_1 \\ L_2 \end{bmatrix} \quad (7)$$

wherein $L_{1,2}(l) = \int_l c_{1,2}(x,y) dl$, $g_H$ is a projection datum with high spectra along path l, $g_L$ is a projection datum with low spectra along path l, $c_{1,2}(x, y)$ is how much the tissue at voxel x, y is like basis material 1 or 2, $\overline{\mu}_H^1$ is a linear attenuation coefficient for basis material 1 averaged over the high (H) spectrum, $\overline{\mu}_L^1$ is a linear attenuation coefficient for basis material 1 averaged over the low (L) spectrum, $\overline{\mu}_H^2$ is a linear attenuation coefficient for basis material 2 averaged over the high (H) spectrum, $\overline{\mu}_L^2$ is a linear attenuation coefficient for basis material 2 averaged over the low (L) spectrum, and $g_{H,L}^{(BH)}$ is beam-hardening perturbation at high (H) or low (L) spectrum and from kV-waveform information.

In step 514, the processing circuitry performs reconstruction, as described below.

In the hybrid photon-counting CT system shown in FIGS. 1 and 2, the third-generation data provides accurate measurement of the energy-integrated attenuation, while the sparse fourth-generation data reflects the attenuation for each of the energy bins. One embodiment of the cost function is shown in equation (8). In the third-generation data fidelity term, a beam-hardening correction term is used to correct a beam-hardening effect that corresponds to the kV used in the measurement.

$$\psi(c) = \sum_{jn} \frac{1}{\sigma_{jn}^2} \left( \sum_i a_{ji} c_n(i) - L_n^{(M)}(j) \right)^2 + \quad (8)$$

$$\underbrace{\phantom{XXXXXXXXXXX}}_{4^{th}\text{-generation PCD term}}$$

$$\sum_j \frac{1}{\sigma_j^2} \left( \sum_{n=1}^{N} L_n(j) \overline{\mu}_{nM} - g_M(j) - g_M^{(BH)}(L) \right)^2 + wV(c)$$

$$\underbrace{\phantom{XXXXXXXXXXX}}_{3^{rd}\text{-generation energy integrated term}} \quad \text{Regularization term}$$

wherein $a_{ji}$ is a system matrix for the fourth-generation CT in polar coordinates, $c_n(i)$ are the basis images, V(c) is the regulation term, $g_M(j)$ is the measured third-generation data, $g_M^{(BH)}(L)$ is the beam-hardening correction, $L_n^{(M)}(j)$ is the fourth-generation data after the decomposition for the nth basis material, $\sigma_j$ and $\sigma_{jn}$ are an noise standard deviation estimation for the third-generation and the fourth generation data, respectively, w is a hyper-parameter for the regularization, $\overline{\mu}_{nM}$ is an average attenuation coefficient for the nth basis material wherein M is an indicator relating to measurement, j is an index for the sinogram rays, i is the index for the basis material image voxels, and n is an index for basis materials.

The cost function is minimized with an iterative procedure to find the spectral images under a positivity constraint.

Figure 6:
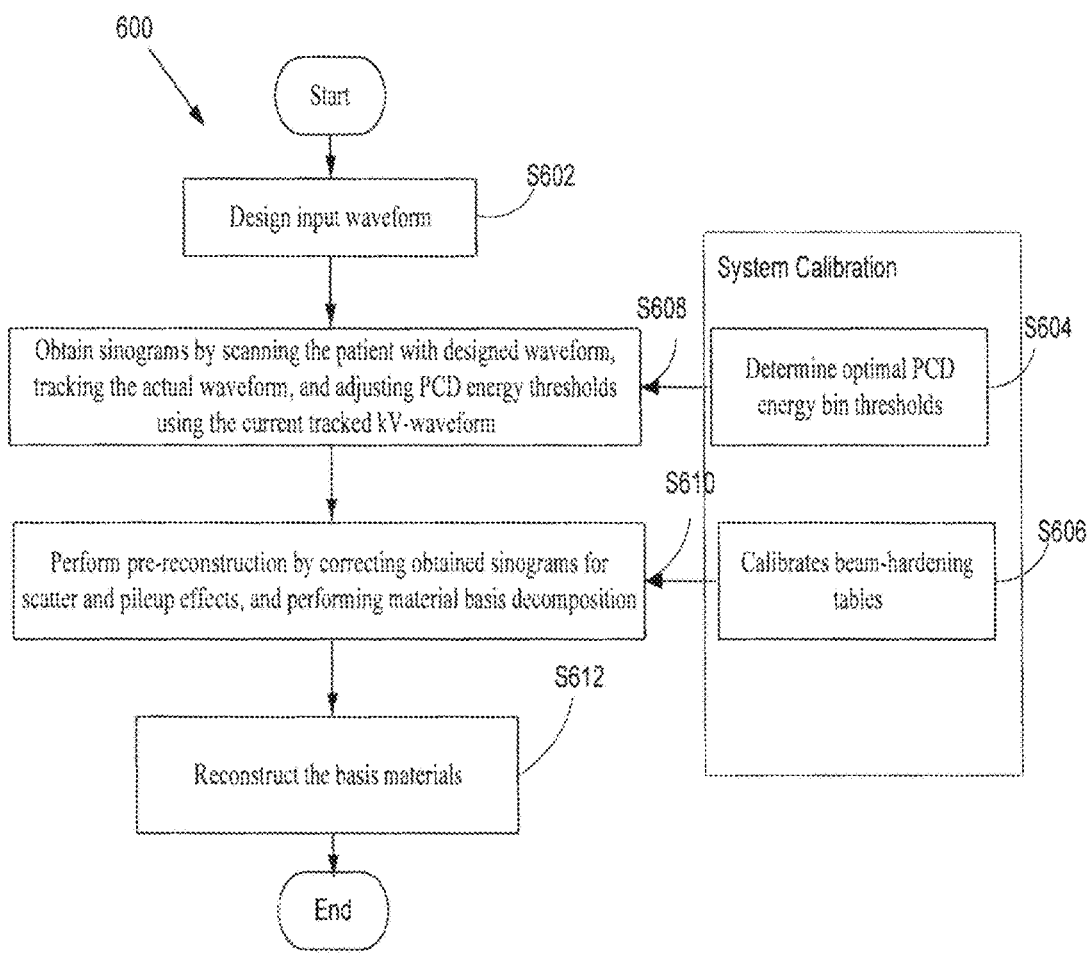

Referring to FIG. 6, a flowchart 600 is shown describing a method for generating a wide X-ray spectrum in a third-generation CT scanner or a hybrid-geometry photon-counting CT scanner with an actual kV-waveform tracking function.

In step 602, a kV and mA waveform is designed to optimize the quality for the scan for a given patient using personal information, such as age, size, gender, and the diagnostic task. This design step is similar to step 602.

In step 604, during system calibration, the processing circuitry determines optimal photon-counting detector (PCD) energy bins for each kV value used, so that the noise of the measurement in each bin is equalized on average. This can be done using either simulation or phantom measurements. In other words, in this step, the energy ranges of each bin are set.

In step 606, during the system calibration, the processing circuitry calibrates beam-hardening tables for all desired kV and transition states.

In step 608, the processing circuitry obtains sinograms by scanning the patient with the designed kV-waveform, tracking the actual kV-waveform during the scan, and adjusting the PCD energy thresholds for the actual kV-waveform. Compared with step 510, step 608 tracks the actual kV-waveform during the scan, and adjusts the PCD energy thresholds for the actual tracked kV-waveform instead of using the verified kV-waveform. In particular, a reference detector is placed near the X-ray tube to directly measure the source flux. Additional photon-counting detectors can also be added as a reference to measure both source flux and spectrum. Alternatively, the voltage waveform from the output of the high voltage generator can be directly measured.

In step 610, the processing circuitry performs pre-reconstruction by correcting the sinograms for scatter and pileup effects, and performing material basis decomposition in a projection domain based on the actual recorded kV-waveform and calibrated beam-hardening tables. This step is similar to step 512, except the actual recorded kV-waveform is used for the pre-reconstruction instead of the verified kV-waveform.

In step 612, the processing circuitry performs reconstruction. This step is similar to step 514.

Figure 9A:
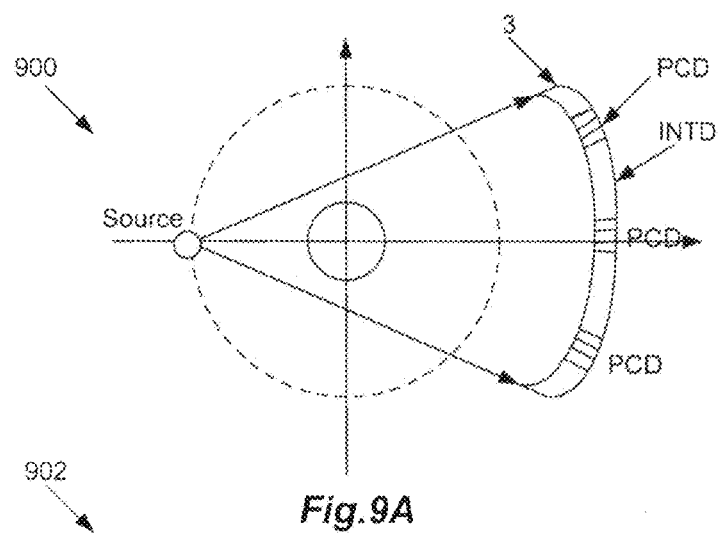
FIG. 9A illustrates an exemplary third-generation CT scanner with a hybrid detector.
Figure 9B:
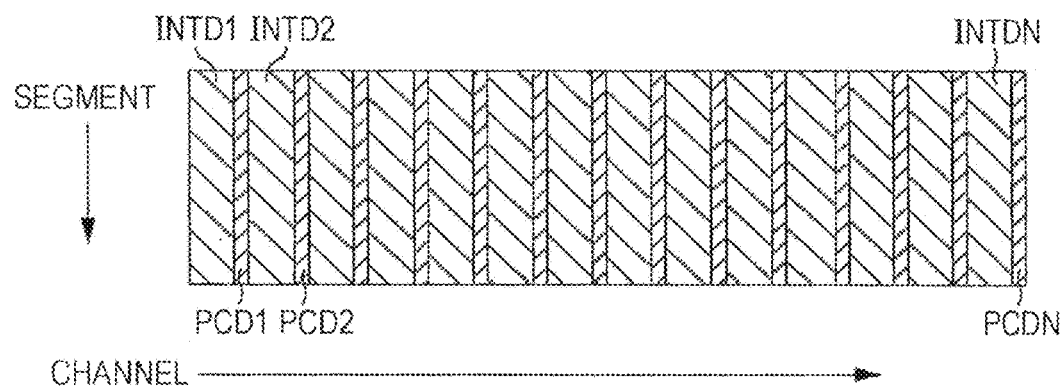
FIG. 9B shows one embodiment of a basic hybrid detector in the CT system.

FIG. 9A illustrates a third-generation CT with a hybrid detector 900. Compared with the CT system described in FIG. 1, the detector 3 is implemented with a hybrid detector. FIG. 9B illustrates one embodiment of a basic hybrid detector in the CT scanner system. In one embodiment of the hybrid detector, the detector array 902 includes a plurality of photon-counting detectors (PCDs) and integrating detectors (INTD) in a predetermined alternating pattern. The detector elements are placed in the segment direction and the channel direction as respectively indicated by the arrows in the detector array 902. Along the channel direction, the photon counting detectors (or the photon counting detectors are sparsely and equidistantly placed at the fixed positions in one embodiment according to the current invention. In the illustrated embodiment, the integrating detector (INTD) units or the integrating detectors (INTD) are placed between the two adjacent ones of the photon counting detectors except one on the first integrating detector unit INTD1. Because of the above difference in the channel size, the photon counting detectors are sparsely located in the channel direction with respect to the integrating detectors (INTD).

The hybrid detector is used in the detector in the third-generation geometry such as shown in FIG. 9A. The detector array 902 forms an arc whose middle portion is centered at a predetermined X-ray source in third-generation CT geometry.

The proposed methods can be implemented in the third- and fourth-generation hybrid photon-counting CT system shown in FIG. 2 and a third-generation CT with the hybrid detector shown in FIG. 9A. These methods are expected to generate more uniform noise in monoenergetic images compared to conventional systems, especially in the third- and fourth-generation hybrid photon-counting CT system and the third-generation CT system with the hybrid detector.

Figure 10:
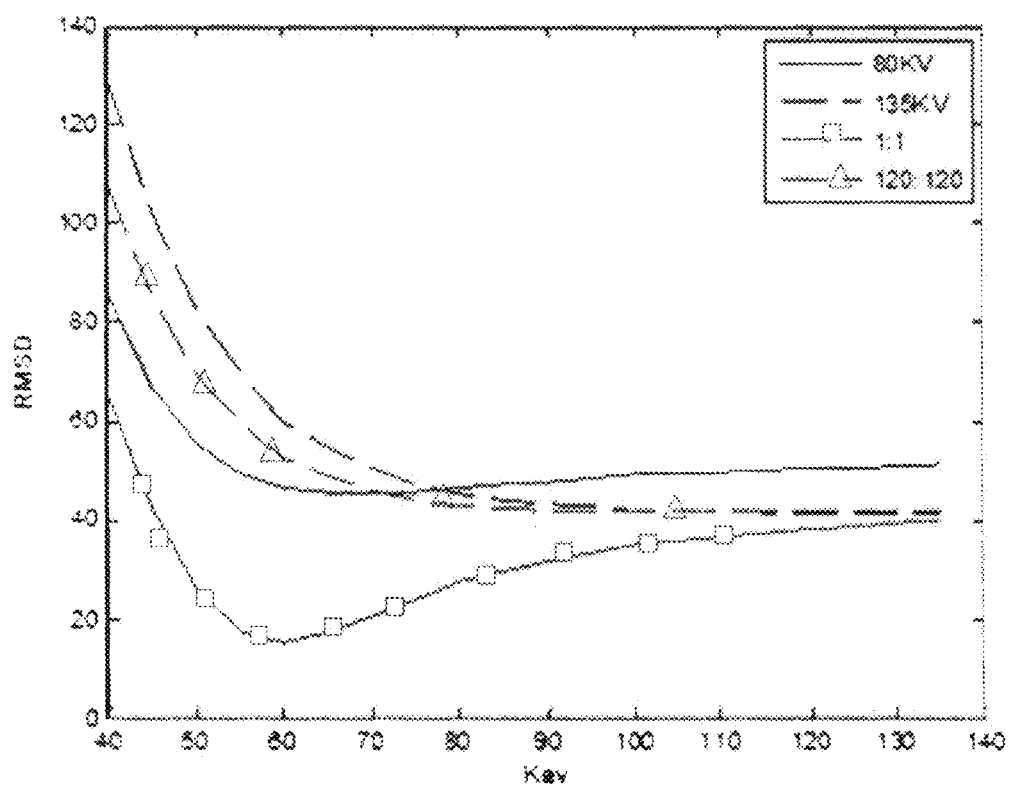
FIG. 10 shows an improvement of noise performance using a kV switching method on a hybrid photon-counting CT.

FIG. 10 shows the improvement of noise performance using a kV switching method on the hybrid photon counting CT. The horizontal axis is the energy of the virtual monoenergetic image, and the vertical axis is the noise standard deviation in the image. Four different source spectra were used: 80 kVp, 135 kVp are the conventional X-ray spectra, while 1:1 and 120:120 are the disclosed wide spectra using square kV waveform switching between 80 kVp and 135 kVp, at the frequency of 1 view or 120 views, respectively. The noise standard deviation of the 1:1 wide spectra is significantly lower than the 80 kVp and 135 kVp conventional X-ray spectra.

Figure 11:
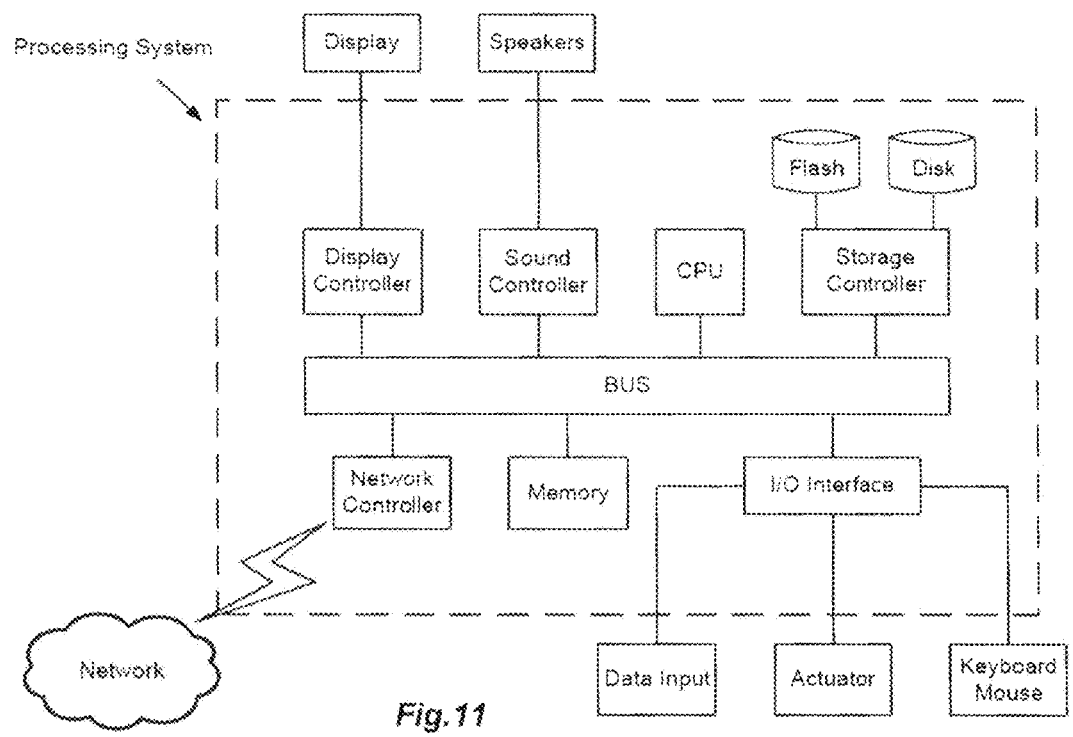
FIG. 11 shows a schematic diagram of an exemplary processing system.

An exemplary processing system is illustrated in FIG. 11, which is an exemplary implementation of the system shown in FIGS. 1 and 2. The system controller 210 and the reconstruction device 214 can each be a hardware device, e.g., a CPU that has been specifically configured to execute one or more computer programs that cause the CPU to perform the functions illustrated in the flowcharts of FIGS. 5-6. In particular, this exemplary processing system can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) imaging apparatus, comprising:
 a radiation source configured to emit X-rays;
 a plurality of photon-counting detectors configured to detect the X-rays emitted by the radiation source and generate a photon counting signal based on the detected X-rays; and
 processing circuitry configured to
  obtain a kV-waveform used by the radiation source to generate the X-rays during a scan of an object, and
  adjust at least one energy threshold dividing the photon counting signal into a plurality of spectral bins in accordance with the obtained kV-waveform so that detected photon counts in the respective spectral bins are substantially equalized.

2. The apparatus of claim 1, wherein the processing circuitry is further configured to perform a material basis decomposition in accordance with the plurality of spectral bins.

3. The apparatus of claim 2, wherein the processing circuitry is further configured to perform the material basis decomposition in accordance with the obtained kV-waveform and at least one beam-hardening table.

4. The apparatus of claim 1, further comprising: a plurality of energy-integrating detectors configured to rotate together with the radiation source, wherein the plurality of photon-counting detectors are arranged at fixed, sparsely distributed positions.

5. The apparatus of claim 1, further comprising: a plurality of energy-integrating detectors configured to rotate together with the radiation source, wherein the photon-counting detectors are sparsely distributed among the energy-integrating detectors.

6. The apparatus of claim 1, wherein the processing circuitry is further configured to perform a system calibration, which determines the at least one energy threshold dividing the photon counting signal into the plurality of spectral bins and determines at least one beam-hardening table.

7. The apparatus of claim 1, wherein
 the radiation source is further configured to emit the X-rays with an energy spectrum corresponding to a desired kV-waveform,
 the desired kV-waveform is a square wave that switches between a first voltage level and a second voltage level of the X-ray source in accordance with a period and a duty cycle of the square wave, and
 the second voltage level is different from the first voltage level.

8. The apparatus of claim 7, wherein the desired kV-waveform is determined by maximizing dose efficiencies for the object to be scanned.

9. The apparatus of claim 7, wherein the processing circuitry is further configured to obtain the obtained kV-waveform by measuring a voltage of the X-ray source while performing an air scan during which the X-ray source is controlled according to the desired kV-waveform, and verify the obtained kV-waveform in comparison with the desired kV-waveform.

10. The apparatus of claim 1, wherein the processing circuitry is further configured to obtain the obtained kV-waveform by measuring a voltage of the X-ray source during the scan of the object.

11. The apparatus of claim 6, wherein the processing circuitry is further configured to obtain raw sinogram data during the scan of the object, and perform pre-reconstruction by correcting the obtained raw sinogram data for scatter and pileup effects.

12. The apparatus of claim 11, wherein the processing circuitry is further configured to perform the scatter and pileup correction using the raw sinogram data, a linear detector response scatter component, a nonlinear detector response scatter component, and a nonlinear detector response pileup component.

13. A computed tomography (CT) imaging method, comprising:
obtaining a kV-waveform used by a radiation source to generate X-rays during a scan of an object; and
adjusting at least one energy threshold dividing a photon counting signal obtained from a photon-counting detector into a plurality of spectral bins in according with the obtained kV-waveform so that detected photon counts in the respective spectral bins are substantially equalized.

14. The method of claim of claim 13, further comprising performing a material basis decomposition in accordance with the plurality of spectral bins.

15. The method of claim 13, further comprising scanning the object using a desired kV-waveform, wherein the desired kV-waveform is a square wave that switches between a first voltage level and a second voltage level of the X-ray source in accordance with a period and a duty cycle of the square wave, wherein the second voltage level is different from the first voltage level.

16. The method of claim 14, wherein the obtaining of the obtained kV-waveform further comprises obtaining the obtained kV-waveform by measuring a voltage of the X-ray source while performing an air scan during which the X-ray source is controlled according to the desired kV-waveform, and verifying the obtained kV-waveform in comparison with the desired kV-waveform.

17. The method of claim 13, wherein the obtaining of the obtained kV-waveform further comprises measuring a voltage of the X-ray source during the scan of the object.

18. The method of claim 13, further comprising:
performing a system calibration by determining the at least one energy threshold and determining at least one beam-hardening table.

19. A non-transitory computer-readable medium storing executable instructions, which when executed by a computer processor, cause the computer processor to execute a method comprising:
obtaining a kV-waveform used by a radiation source to generate X-rays during a scan of an object; and
adjusting at least one energy threshold of energy which divides a photon counting signal obtained from a photon-counting detector into a plurality of spectral bins in accordance with the obtained kV-waveform so that detected photon counts in the respective spectral bins are substantially equalized.

20. The method of claim 19, further comprising:
performing a material basis decomposition in accordance with the plurality of spectral bins.

* * * * *